United States Patent
Pati et al.

(10) Patent No.: US 11,688,061 B2
(45) Date of Patent: Jun. 27, 2023

(54) INTERPRETATION OF WHOLE-SLIDE IMAGES IN DIGITAL PATHOLOGY

(71) Applicant: INTERNATIONAL BUSINESS MACHINES CORPORATION, Armonk, NY (US)

(72) Inventors: Pushpak Pati, Zurich (CH); Guillaume Jaume, Zurich (CH); Antonio Foncubierta Rodriguez, Zurich (CH); Maria Gabrani, Thalwil (CH)

(73) Assignee: International Business Machines Corporation, Armonk, NY (US)

( * ) Notice: Subject to any disclaimer, the term of this patent is extended or adjusted under 35 U.S.C. 154(b) by 358 days.

(21) Appl. No.: 16/953,377

(22) Filed: Nov. 20, 2020

(65) Prior Publication Data

US 2022/0164946 A1 May 26, 2022

(51) Int. Cl.
*G06T 7/00* (2017.01)
*G16H 30/40* (2018.01)
(Continued)

(52) U.S. Cl.
CPC ............ *G06T 7/0012* (2013.01); *G06F 16/54* (2019.01); *G06V 20/695* (2022.01); *G16H 10/40* (2018.01);
(Continued)

(58) Field of Classification Search
CPC ......... G06T 7/0012; G06T 2207/20072; G06T 2207/20081; G06T 2207/20084;
(Continued)

(56) References Cited

U.S. PATENT DOCUMENTS

| 9,117,256 | B2 | 8/2015 | Soenksen | |
|---|---|---|---|---|
| 2020/0302603 | A1* | 9/2020 | Barnes | G06T 7/162 |
| 2022/0367053 | A1* | 11/2022 | Mahmood | G16H 50/20 |

FOREIGN PATENT DOCUMENTS

WO 2017087415 A1 5/2017

OTHER PUBLICATIONS

Densely-Connected Multi-Magnification Hashing for Histopathological Image Retrieval (Year: 2019).*
(Continued)

*Primary Examiner* — Vu Le
*Assistant Examiner* — Winta Gebreslassie
(74) *Attorney, Agent, or Firm* — L. Jeffrey Kelly

(57) ABSTRACT

Computer-implemented methods and systems are provided for interpreting a whole-slide image of a tissue specimen. Such a method includes detecting biological entities in a region of interest independently at each magnification level in a whole-slide image. An entity graph is generated for each magnification level, the entity graph comprising nodes, representing respective biological entities detected at that magnification level, interconnected by edges representing interactions between entities. The method also includes, for each region of interest, generating a hierarchical graph, defining a hierarchy of the entity graphs for that region, in which nodes of different entity graphs are interconnected by hierarchical edges representing hierarchical relations between nodes of the entity graphs. The method further comprises supplying the hierarchical graph for the region to an AI system to produce result data corresponding to a medical evaluation of the tissue specimen represented thereby, and outputting the result data for the tissue specimen.

25 Claims, 9 Drawing Sheets

(51) Int. Cl.
  *G16H 10/40* (2018.01)
  *G16H 50/20* (2018.01)
  *G06F 16/54* (2019.01)
  *G06V 20/69* (2022.01)

(52) U.S. Cl.
  CPC ............. *G16H 30/40* (2018.01); *G16H 50/20* (2018.01); *G06T 2207/20072* (2013.01); *G06T 2207/20081* (2013.01); *G06T 2207/20084* (2013.01); *G06T 2207/30024* (2013.01)

(58) Field of Classification Search
  CPC . G06T 2207/30024; G06T 2207/10056; G06T 2207/20021; G06T 2207/20016; G06T 3/4046; G16H 10/40; G16H 50/20; G16H 30/40; G06F 16/54; G06V 20/695; G06N 3/082; G06N 20/00
  See application file for complete search history.

(56) References Cited

OTHER PUBLICATIONS

Computerized Image-Based Detection and Grading of Lymphocytic Infiltration in HER2+ Breast Cancer Histopathology (Year: 2009).*
Ali et al., "Spatially Aware Cell Cluster (SpACCl) Graphs: Predicting Outcome in Oropharyngeal p16+ Tumors," MICCAI 2013, Lecture Notes in Computer Science, vol. 8149, Springer, Bedin, Heidelberg. https://doi.org/10.1007/978-3-642-40811-3_52, pp. 412-419.
Anand et al., "Histographs: Graphs in Histopathology," arXiv:1908.05020v1 [eess.IV] Aug. 14, 2019, 5 pages.
Bera et al., "Arlilicial intelligence in digital pathology—new tools for diagnosis and precision oncology," Nat Rev Clin Oncol Nov. 2019; 16(11): 703-715. doi:10.1038/s41571-019-0252-y. 30 pages.
Chen et al., "Pathomic Fusion: An Integrated Framework for Fusing Histopathology and Genomic Features for Cancer Diagnosis and Prognosis." arXiv:1912.08937v3 [cs.CV] Sep. 3, 2020, 21 pages.
Doshi-Velez et al., "Towards a Rigorous Science of Interpretable Machine," arXiv:1702.08608v2 [stat.ML] Mar. 2, 2017, 13 pages.
Grace Period Disclosure: Jaume et al., "Towards Explainable Graph Representations in Digital Pathology," arXIV:2007.00311v1 [cs.CV] Jul. 1, 2020, 5 pages.
Grace Period Disclosure: Pati et al., "HACT-Net: A Hierarchical Cell-to-Tissue Graph Neural Network for Histopathological Image Classification," arXIV: 2007. 00584v1 [cs.CV] Jul. 1, 2020, 8 pages.
Graziani et al., "Regression Concept Vectors for Bidirectional Explanations in Histopathology," Proceedings of the First International Workshop of Interpretability of Machine Intelligence in Medical Image Computing at MICCAI 2018, arXiv:1904.04520v1 [cs.LG] Apr. 9, 2019, 9 pages.
Madabhushi et al., "Image Analysis and Machine Learning in Digital Pathology: Challenges and Opportunities," Med Image Anal. Oct. 2016 ; 33: 170-175, doi:10.1016/j.media.2016.06.037, 14 pages.
Sharma et al., "A review of graph-based methods for image analysis in digital histopathology," Diagnostic Pathology 2015, 1:61, ISSN 2364-4893 DOI: http://dx.doi.org/10.17629/www.diagnosticpathology.eu-2015-1:61, 51 pages.
Sharma et al., "Cell nuclei attributed relational graphs for efficient representation and classification of gastric cancer in digital histopathology," SPIE Medical Imaging 2016: Digital Pathology, 9791 (Mar. 23, 2016); doi: 10.1117/12.2216843, pp. 97910X-1-97910X-19.
Wang et al., "Weakly Supervised Prostate TMA Classification Via Graph Convolutional Networks," arXiv:1910.13328v2 [cs.CV] Nov. 6, 2019, 6 pages.
Yener, Cell-Graphs: Image-Driven Modeling of Structure-Function Relationship. Communications of the ACM, Jan. 2017, vol. 60, No. 1, DOI:10.1145/2960404, pp. 74-84.
Ying et al., "GNNExplainer: Generating Explanations for Graph Neural Networks," 33rd Conference on Neural Information Processing Systems (NeurIPS 2019), arXiv:1903.03894v4 [cs.LG] Nov. 13, 2019, 13 pages.
Zhou et al., "CGC-net: Cell Graph Convolutional Network for Grading of Colorectal Cancer Histology Images." arXiv:1909.01068v1 [eess.IV] Sep. 3, 2019, 11 pages.
Mell et al., "The NIST Definition of Cloud Computing", National Institute of Standards and Technology, Special Publication 800-145, Sep. 2011, 7 pages.

* cited by examiner

INTERPRETATION OF WHOLE-SLIDE IMAGES IN DIGITAL PATHOLOGY

The following disclosures are submitted under 35 U.S.C. 102(b)(1)(A): "HACT-Net: A Hierarchical Cell-to-Tissue Graph Neural Network for Histopathological Image Classification", Pushpak Pati et al., arXiv:2007.00584v1 [cs.CV], 1 Jul. 2020; and "Towards Explainable Graph Representations in Digital Pathology", Guillaume Jaume et al., arXiv: 2007.00311v1 [cs.CV], 1 Jul. 2020.

BACKGROUND

The present invention relates generally to interpretation of whole-slide images in digital pathology. Computer-implemented methods are provided for interpreting whole-slide images of tissue specimens, together with systems and computer program products implementing such methods.

The workflow for pathologists to diagnose and plan treatment for various diseases is based on the analysis of disease tissue specimens from macroscopic to microscopic level. Analysis is conventionally performed by inspecting slides of tissue specimens (with one or more stainings to highlight tissue parts) through a microscope from low magnification to high magnification, in that specific order. With recent advances in scanning technology, digital pathology is gaining acceptance by pathologists. The workflow remains the same, but visual inspection is now performed through a screen that renders the so-called "whole-slide image" (WSI) of a tissue specimen. A WSI is a digitized microscopy image taken at multiple different magnification levels. Given the tissue heterogeneity, tissue polymorphism and the large amount of data that is contained in the multiple magnification levels of a WSI, the task is very tedious, time-consuming and prone to inter- and intra-observer variability.

AI (Artificial Intelligence) has potential to assist in the process of analyzing and interpreting digital images of tissue specimens. For example, machine learning models can be trained to detect cells in stained tissue samples and classify cells as healthy or diseased based on features such as size, shape, color, cell distribution, and so on. The most powerful AI image analysis systems employ CNNs (Convolutional Neural Networks). However, convolutional filters are not intuitive and depart from the biological reasoning that underpins pathological decisions. Learning cannot be guided by pathological prior knowledge, and the fixed-size, patch-based learning approach in CNNs suffers from a trade-off between capturing context information and computational complexity. In an attempt to address these issues, the histopathological structure of tissues has been represented by cell-graphs (see "Cell-Graphs: Image-Driven Modeling of Structure-Function Relationship", B. Yener, ACM Communications, Vol. 80, No. 1, 2017) in which cells and cellular interactions are respectively represented by nodes and edges of a graph. Graph Neural Networks (GNNs) have also been proposed to apply powerful graph convolutions for extracting relational information from cell-graphs in histopathology (see "CGC-Net: Cell Graph Convolutional Network for Grading of Colorectal Cancer Histology Images", Y. Zhou et al., IEEE/CVF International Conference on Computer Vision Workshop, 2019). These cell-graph techniques are restricted to analysis of cells and clusters of cells.

Improved techniques for AI-assisted WSI interpretation in digital pathology would be highly desirable.

SUMMARY

One aspect of the present invention provides a computer-implemented method for interpreting a whole-slide image of a tissue specimen. The method includes, for at least one region of interest in the tissue specimen, detecting biological entities in that region independently at each of a plurality of magnification levels in the whole-slide image. An entity graph is generated for each magnification level, the entity graph comprising nodes, representing respective biological entities detected at that magnification level, interconnected by edges representing interactions between entities represented by the nodes. The method also includes, for the or each region of interest, generating a hierarchical graph, defining a hierarchy of the entity graphs for that region, in which nodes of different entity graphs are interconnected by hierarchical edges representing hierarchical relations between nodes of the entity graphs for the region. The method further comprises supplying the hierarchical graph for the at least one region to an AI system which is adapted to process such hierarchical graphs to produce result data corresponding to a medical evaluation of the tissue specimen represented thereby, and outputting the result data for the tissue specimen.

Methods embodying the invention use a hierarchical graph representation for regions of interest in a tissue specimen. The hierarchical graph is constructed from the set of entity graphs representing biological entities which are independently detected at a plurality of different magnification levels in the whole-slide image. Different biological entities (such as nuclei, cells, tissue parts, whole tissues, glands, etc.,) can be detected at different magnification levels, and the hierarchical graph can model morphology and topology of entities across multiple levels to reflect the hierarchical nature of the tissue itself. Not only cellular information, but also tissue distribution information such as stromal microenvironment, tumor microenvironment, lumen structure, etc., can be represented in the hierarchical graph. Vital information available across multiple resolutions of the tissue can thus be accommodated for more accurate representation of histopathological structures. Analysis of the resulting hierarchical graph (or graphs) in the AI system conforms more closely with clinical diagnostic procedure for analyzing tissue at progressive magnification levels, exploiting available information throughout the hierarchical tissue structure. The results of the AI processing correspond to a medical evaluation such as a classification (e.g. diseased or healthy), grading (e.g. on a severity scale), or other such evaluation of the tissue specimen. Methods embodying the invention thus offer more comprehensive and reliable interpretation of whole slide images for more accurate, AI-assisted evaluation of tissue specimens. Moreover, the hierarchical graph representation scales easily across all magnification levels, offering compact representations which can be efficiently processed for evaluation, even at the whole-slide level.

The AI system may be adapted to process the hierarchical graph for a single region of interest. The method then includes, for the or each region of interest, supplying the hierarchical graph for that region to the AI system to obtain result data corresponding to a medical evaluation of that region of the tissue specimen. This allows individual interpretation of a specific region or regions, whereby a pathological decision may be based on region-specific results for a specimen. In addition, or as an alternative, preferred embodiments provide for evaluation at the whole-slide level. In these embodiments, the method includes generating a hierarchical graph for each of a plurality of regions of interest, and generating a region connectivity graph which comprises nodes, representing respective regions of interest, interconnected by edges representing spatial relations between the regions represented by those nodes. The method also generates a whole-slide graph in which the hierarchical graph for each region is associated with the node representing that region in the region connectivity graph. The whole-slide graph is then supplied to the AI system which is adapted to process the whole-slide graph to produce result data corresponding to a medical evaluation of the whole-slide image of the tissue specimen.

Particularly preferred methods include supplying the hierarchical graph for the (or each) region of interest, or the whole slide graph where provided, to a graph pruning model along with the corresponding result data from the AI system. The graph pruning model is adapted to process the hierarchical (or whole-slide) graph to produce a minimized subgraph which, when supplied to the AI system, produces subgraph result data which correlates maximally with the original result data. In these embodiments, the graph pruning model serves as a "post-hoc explainer". The subgraph represents those features of the original graph which were most significant for the evaluation result produced for the graph, and thus provides an explanation for the decision process in the AI system. Such subgraphs offer efficient, human-comprehensible representations of the reasoning underlying evaluations, adding interpretability to operation of the AI system.

A further aspect of the invention provides a computing system for interpreting a whole-slide image of a tissue specimen. The system includes memory for storing the whole-slide image, and image processing logic which is adapted, for at least one region of interest in the tissue specimen, to detect biological entities in that region independently at each of a plurality of magnification levels in the whole-slide image. The computing system also includes entity graph logic which is adapted, for each magnification level, to generate an entity graph as described above, and hierarchical graph logic which is adapted, for the or each region of interest, to generate a hierarchical graph as described above. The computing system further comprises an AI system which is adapted to process the hierarchical graph (or graphs) to produce result data corresponding to a medical evaluation of the tissue specimen represented thereby, and to output the result data for the tissue specimen.

In embodiments where the AI system produces a region-specific evaluation for a particular region of interest, the AI system may comprise a pre-trained machine learning model comprising a graph neural network, which is adapted to process the hierarchical graph for a region of interest to produce embedded data representing the hierarchical graph, and an evaluator (such as a machine learning classification or regression model) which is adapted to map the embedded data to the result data for the region.

Preferred embodiments of the computing system are adapted to evaluate specimens at the whole-slide level and can generate a hierarchical graph for each of a plurality of regions of interest. These embodiments include whole-slide graph logic which is adapted to generate a region connectivity graph and a whole-slide graph as respectively defined above, and the AI system is adapted to process the whole-slide graph to produce result data corresponding to a medical evaluation of the whole-slide image. This AI system may comprise a graph neural network which is adapted to process the whole-slide graph to produce embedded data representing the whole-slide graph, and an evaluator adapted to map the embedded data to the result data for the whole-slide image.

Efficient implementations of the above-mentioned graph neural networks are described in detail below. Preferred embodiments also include a graph pruning model implementing the post-hoc explainer described earlier.

A further aspect of the invention provides a computer program product comprising a computer readable storage medium embodying program instructions, executable by a computing system, to cause the computing system to perform a method for interpreting a whole-slide image as described above.

Embodiments of the invention will be described in more detail below, by way of illustrative and non-limiting examples, with reference to the accompanying drawings.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

Embodiments to be described can be performed as computer-implemented methods for interpreting whole-slide images of tissue specimens. The methods may be implemented by a computing system comprising one or more general- or special-purpose computers, each of which may comprise one or more (real or virtual) machines, providing functionality for implementing operations described herein. Steps of methods embodying the invention may be implemented by program instructions, e.g., program modules, implemented by a processing apparatus of the system. Generally, program modules may include routines, programs, objects, components, logic, data structures, and so on that perform particular tasks or implement particular abstract data types. The computing system may be implemented in a distributed computing environment, such as a cloud computing environment, where tasks are performed by remote processing devices that are linked through a communications network. In a distributed computing environment, program modules may be located in both local and remote computer system storage media including memory storage devices.

Figure 1:
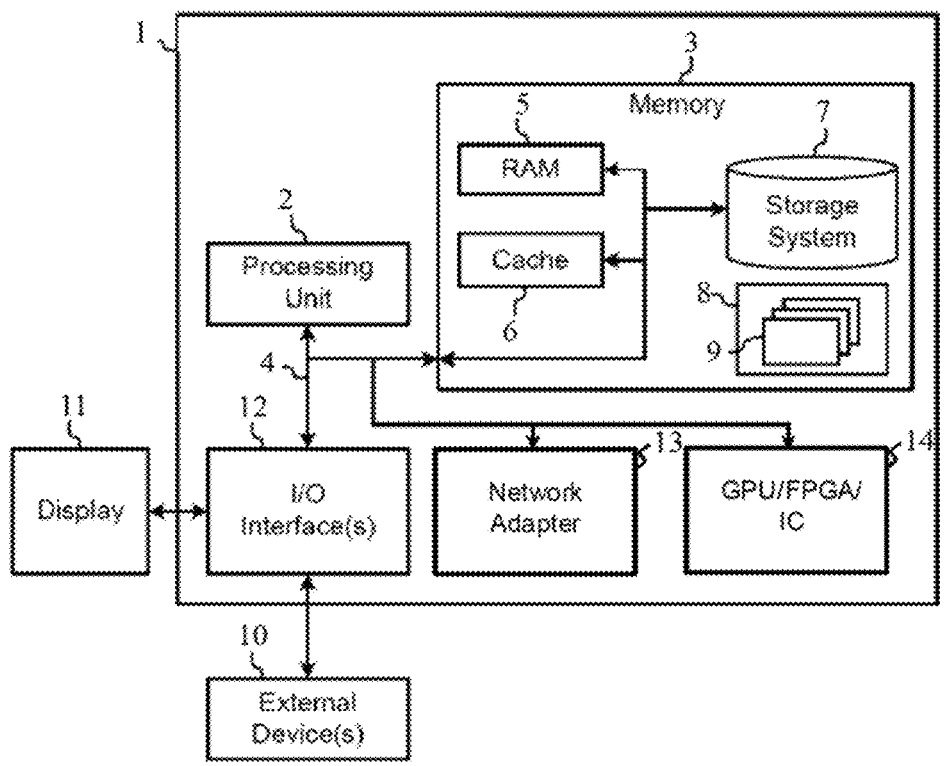
FIG. 1 is a schematic representation of a computing system for implementing methods embodying the invention.

FIG. 1 is a block diagram of exemplary computing apparatus for implementing methods embodying the invention. The computing apparatus is shown in the form of a general-purpose computer 1. The components of computer 1 may include processing apparatus such as one or more processors represented by processing unit 2, a system memory 3, and a bus 4 that couples various system components including system memory 3 to processing unit 2.

Bus 4 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer 1 typically includes a variety of computer readable media. Such media may be any available media that is accessible by computer 1 including volatile and non-volatile media, and removable and non-removable media. For example, system memory 3 can include computer readable media in the form of volatile memory, such as random access memory (RAM) 5 and/or cache memory 6. Computer 1 may further include other removable/non-removable, volatile/non-volatile computer system storage media. By way of example only, storage system 7 can be provided for reading from and writing to a non-removable, non-volatile magnetic medium (commonly called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can also be provided. In such instances, each can be connected to bus 4 by one or more data media interfaces.

System memory 3 may include at least one program product having one or more program modules that are configured to carry out functions of embodiments of the invention. By way of example, program/utility 8, having a set (at least one) of program modules 9, may be stored in the system memory 3, as well as an operating system, one or more application programs, other program modules, and program data. Each of the operating system, one or more application programs, other program modules, and program data, or some combination thereof, may include an implementation of a networking environment. Program modules 9 generally carry out the functions and/or methodologies of embodiments of the invention as described herein.

Computer 1 may also communicate with: one or more external devices 10 such as a keyboard, a pointing device, a display 11, etc.; one or more devices that enable a user to interact with computer 1; and/or any devices (e.g., network card, modem, etc.) that enable computer 1 to communicate with one or more other computing devices. Such communication can occur via Input/Output (I/O) interfaces 12. Also, computer 1 can communicate with one or more networks such as a local area network (LAN), a general wide area network (WAN), and/or a public network (e.g., the Internet) via network adapter 13. As depicted, network adapter 13 communicates with the other components of computer 1 via bus 4. Computer 1 may also communicate with additional processing apparatus 14, such as one or more GPUs (graphics processing units), FPGAs, or integrated circuits (ICs), for implementing embodiments of the invention. It should be understood that other hardware and/or software components may be used in conjunction with computer 1. Examples include, but are not limited to: microcode, device drivers, redundant processing units, external disk drive arrays, RAID systems, tape drives, and data archival storage systems, etc.

Figure 2:
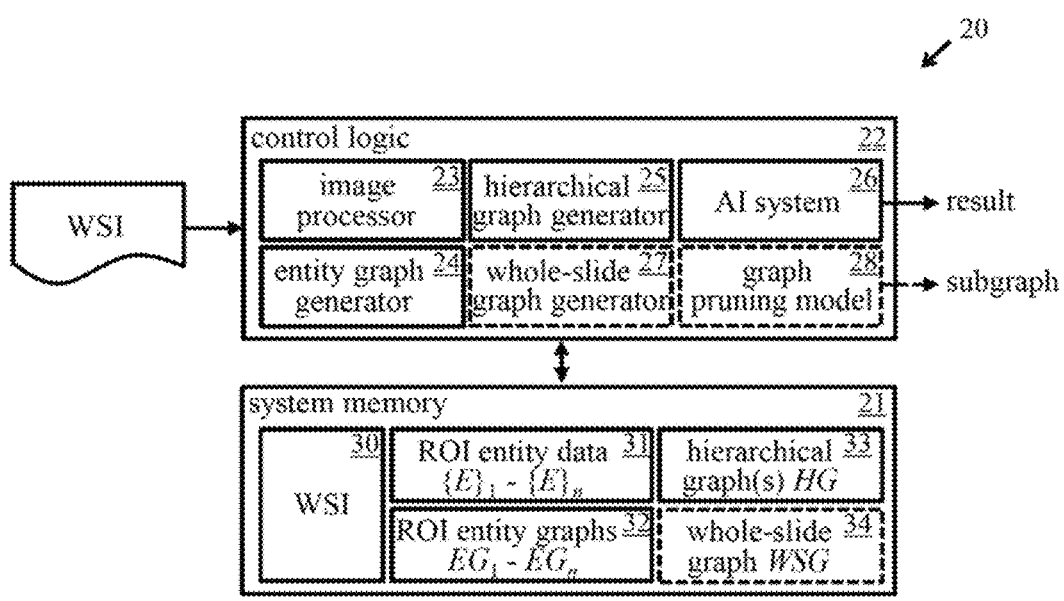
FIG. 2 illustrates component modules of a computing system for interpreting a whole slide image (WSI) according to at least one embodiment.

The FIG. 2 schematic drawing illustrates component modules of an exemplary computing system 20 embodying the invention. The computing system 20 comprises memory 21 and control logic, indicated generally at 22, comprising functionality for interpreting a whole slide image (WSI). Control logic 22 comprises an image processor module 23, an entity graph generator 24, a hierarchical graph generator 25, and an AI system 26. As indicated in dashed lines in the figure, preferred embodiments also include a whole-slide graph generator 27 and a graph pruning model 28. Each of these logic modules 23 through 28 comprises functionality for implementing particular steps of a WSI interpretation method detailed below. These modules interface with memory 21 which stores various data structures used in operation of computing system 20. These data structures include: a WSI 30 for a tissue specimen; entity data 31 for one or more regions of interest (ROIs) in the tissue specimen; a set of entity graphs 32 which are generated for each ROI; and a hierarchical graph 33 for each ROI. Preferred embodiments also store a whole-slide graph 34.

In general, functionality of logic modules 23 through 28 may be implemented by software (e.g., program modules) or hardware or a combination thereof. Functionality described may be allocated differently between system modules in other embodiments, and functionality of one or more modules may be combined. The component modules of computing system 20 may be provided in one or more computers of an interconnected computing system. For example, all modules may be provided in a user computer 1, or modules may be provided in one or more computers/servers to which user computers can connect via a network for input of WSIs to be interpreted. Such a network may in general comprise one or more component networks and/or internetworks, including the Internet. System memory 21 may be implemented by one or memory/storage components associated with one or more computers of computing system 20.

Figure 3:
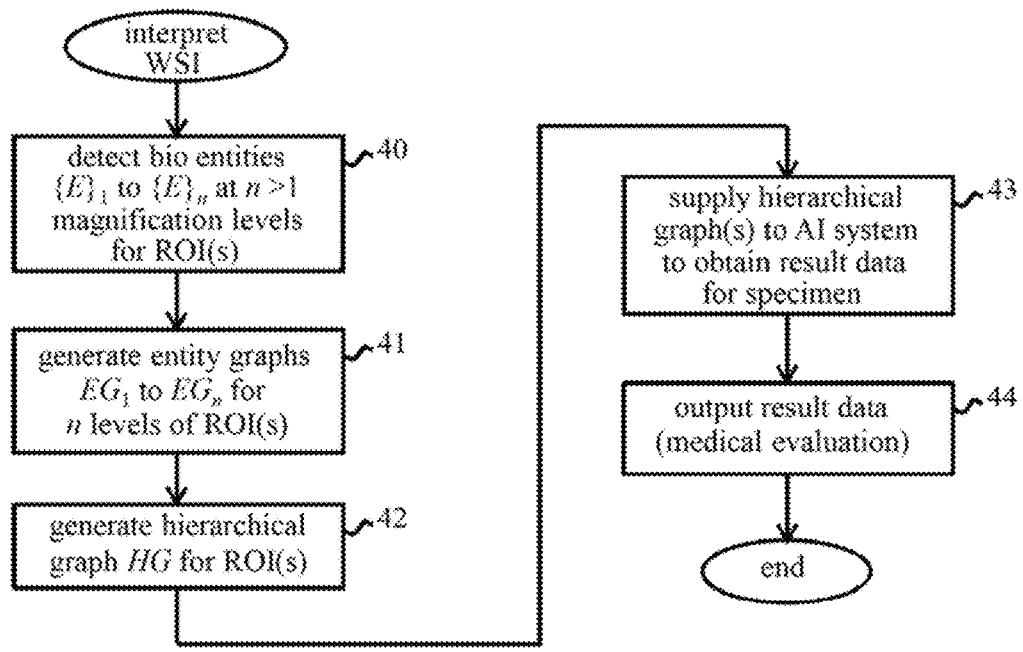
FIG. 3 is a flowchart illustrating a WSI interpretation method embodying the invention.

In operation of computing system 20, a WSI of a tissue specimen is input to the system and stored at 30 in system memory 21. Basic steps of the subsequent WSI interpretation method are indicated in greater detail in FIG. 3. With reference to FIG. 3, in step 40, the image processor 23 processes WSI 30 to detect biological (bio) entities in one or more ROIs in the tissue specimen. The ROI(s) depend on the specific evaluation task to be performed for a tissue specimen, and can be identified by generally known pre-processing steps described below. For the (or each) ROI, image processor 23 detects biological entities apparent in the ROI at each of a plurality n of magnification levels in the WSI. Entities are detected independently at each magnification level, whereby different entities (e.g., nuclei, cells, tissue parts, whole tissues, etc.,) which are apparent at different resolutions can be detected across the various magnification levels of the image. For a given ROI, the set of entities detected at each magnification level i (i=1 to n) is denoted here by {E}i. The value of n for a particular ROI, and the particular magnification levels selected for entity detection, may be predetermined for a given task in some embodiments. In other embodiments, these parameters may be determined automatically by image processor 23 (e.g., based on detection of new entities at particular magnification levels) and/or by user selection based on visualization of ROIs in a user-interface. For each set of entities {E} image processor 23 makes measurements in the image to determine locations of the entities, and preferably also other features, described below, relating to form and distribution of entities. The resulting entity data for the entity sets $\{E\}_1$ to $\{E\}_n$ in the ROI is stored at 31 in system memory 21.

In step 41 of FIG. 3, for each ROI in the specimen, the entity graph generator 24 generates a set of graphs, referred to herein as "entity graphs", one for each magnification level i. The entity graph $EG_i$ for a magnification level i comprises nodes, representing respective biological entities in set $\{E\}_i$ for that magnification level, interconnected by edges representing interactions between entities represented by the nodes. Construction of these entity graphs is explained in detail below. Next, in step 42, the hierarchical graph generator 25 generates a hierarchical graph for each ROI. The hierarchical graph HG for an ROI defines a hierarchy of the entity graphs $EG_1$ to $EG_n$ for that region. As explained further below, the hierarchical graph is generated by interconnecting nodes of different entity graphs $EG_1$ to $EG_n$ by edges (referred to herein as "hierarchical edges") representing hierarchical relations between nodes of these entity graphs.

In step 43, the resulting hierarchical graph (or graphs) are supplied to AI system 26. This AI system is adapted to process such hierarchical graphs to produce result data corresponding to a medical evaluation of the tissue specimen represented thereby. Such an AI system may be implemented by one or a combination of machine learning (ML) and rule-based AI systems. Preferred embodiments employ ML models to exploit the powerful learning capabilities of these systems. ML models can be trained to map input data for an application to an output representing some type of evaluation of the input data, typically to assign the data to one of a predetermined set of classes (classification) or to assign a value to the data on some predetermined scale (regression). Numerous implementations for ML models are known in the art. These models can be trained by exposing the model to a set of training data samples and progressively updating the model parameters to optimize the model for the application in question. Embodiments may use any type of ML model (which may comprise one or more component models) trained to process input hierarchical graph data to produce an output corresponding to the evaluation required for a given task. A combined ML and rule-based system may also be employed in some embodiments. Particularly preferred embodiments employ ML systems based on graph neural networks as illustrated by examples below.

In step 44 of FIG. 3, the result data from AI system 26 is output by computing system 20 for human inspection, e.g., by displaying the result data in a user interface. This result data may provide an evaluation (such as a classification, grading, etc.) of all or part(s) of the tissue specimen represented by the input hierarchical graph(s). Results may thus evaluate a single ROI, or each of set of ROIs, and/or provide an overall evaluation based on multiple ROIs as explained further below.

Figure 4A:
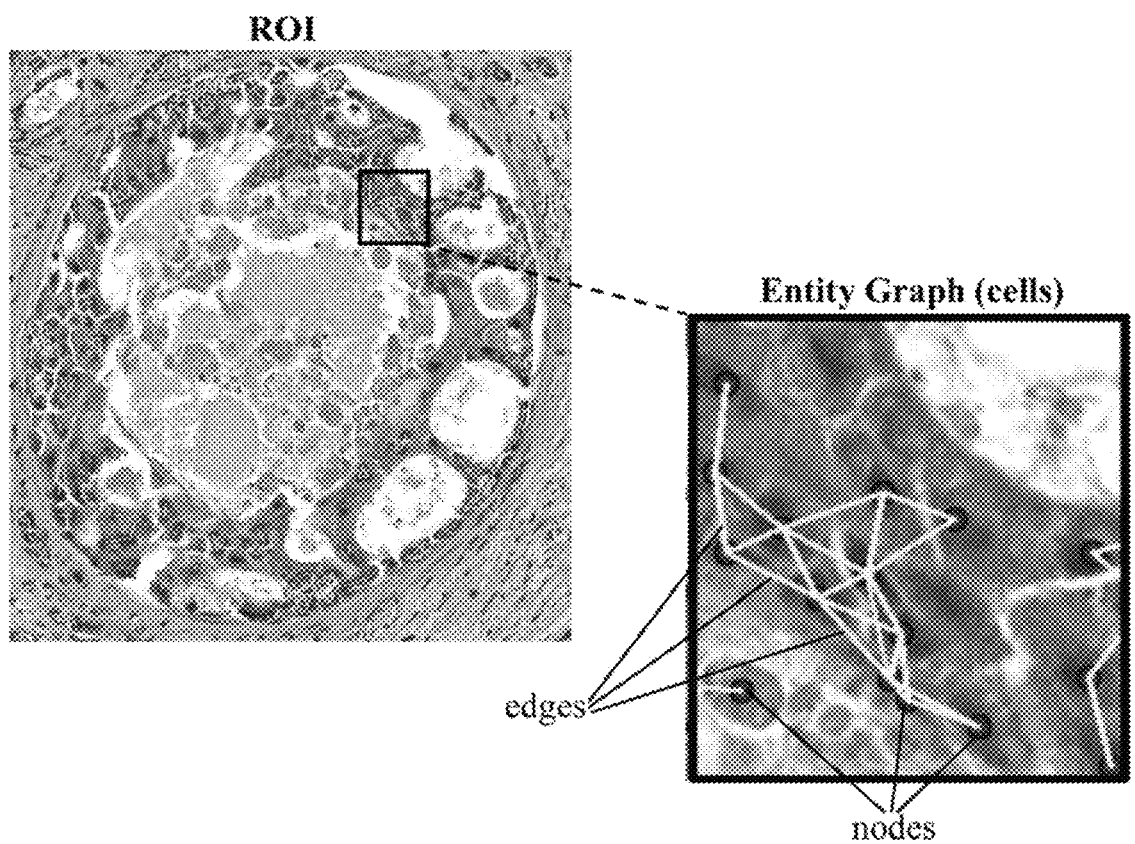
FIGS. 4a through 4c, and FIG. 5, illustrate principles of graph construction in the FIG. 3 method according to at least one embodiment.
Figure 4B:
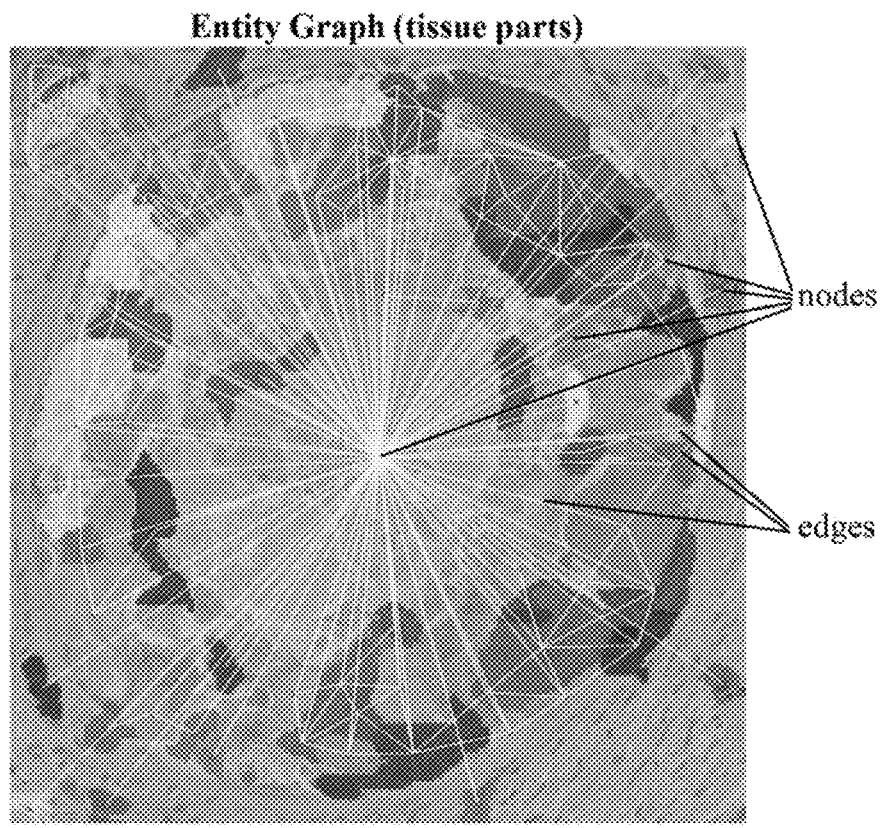

The construction of entity graphs in step 41 of FIG. 3 is illustrated schematically in FIGS. 4a and 4b. FIG. 4a shows an image of an ROI, here a cancer tumor, in a tissue specimen, and the enlargement shows part of an entity graph superimposed on the image. Nodes of the entity graph are indicated by dark dots in the enlargement, and edges by white lines interconnecting pairs of nodes. At this magnification level, nodes correspond to individual cells and edges correspond to cellular interactions. For each cell nucleus detected in the magnified image, image processor 23 makes measurements to determine the location (and preferably other attributes detailed below) of the cell. Locations of cells, and hence nodes of the cell graph, may be defined by the spatial centroids of the nuclei. Edges in this entity graph represent interactions between cells. Interactions can be defined here in dependence on distance between the detected cells. For example, it can be assumed that spatially close cells encode biological interactions and should be connected by an edge in the cell graph, whereas distant cells have weak cellular interactions and should remain disconnected (no edge) in the graph. Various techniques can be envisaged for edge insertion based on distance between cells, and particular examples are described below.

FIG. 4b shows an image of the same ROI with the entity graph for a lower magnification level superimposed on the image. At this magnification level, the entities represented by nodes are different tissue parts (colored in different shades of grey in the figure). In this example, the tissue parts are (all or parts of) areas of different types of tissue in the tumor. Tissue parts may be defined in various ways for a given magnification level as explained further below. Nodes in this entity graph may be located at the spatial centroids of the detected tissue parts. The large central node here depicts the centroid of the surrounding stroma tissue in the tumor. Edges in this entity graph represent interactions among the tissue parts. In the example illustrated, edges were inserted based on distance between tissue parts as described in more detail below.

Figure 4C:
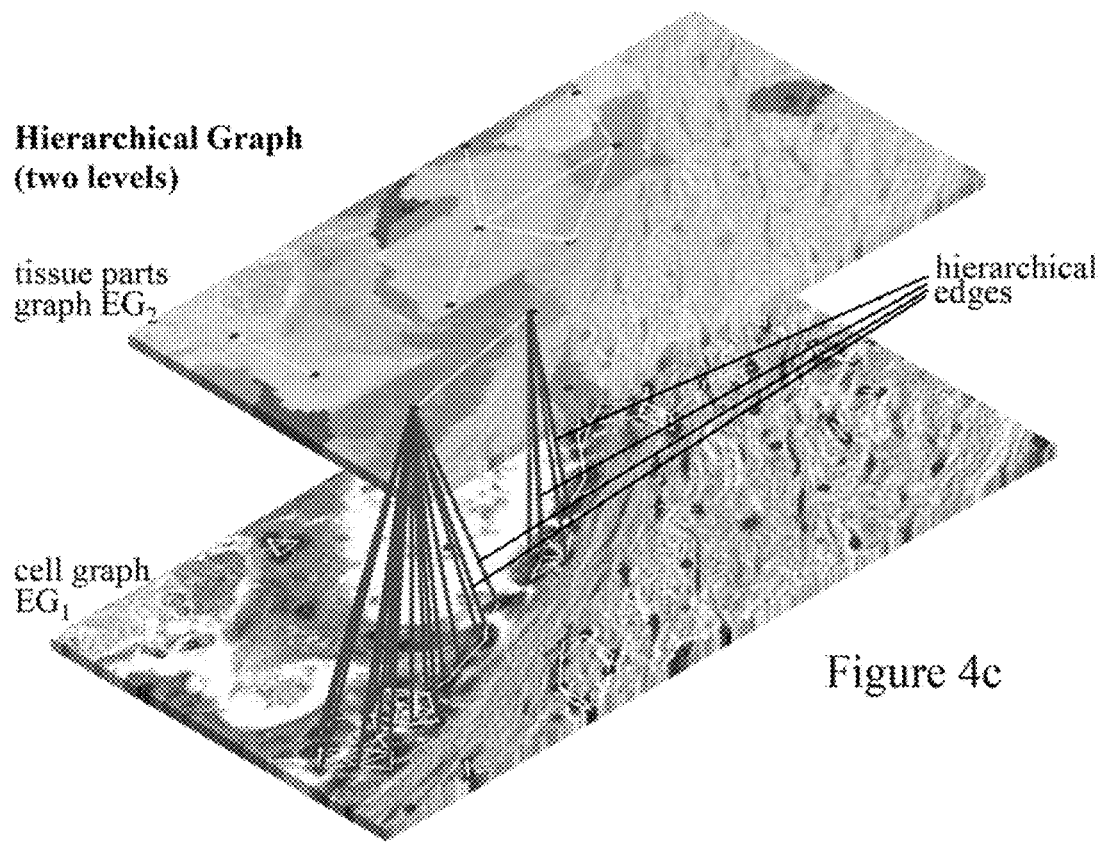

FIG. 4c illustrates construction principles for a two-level hierarchical graph generated from the entity graphs of FIGS. 4a and 4b. This hierarchical graph includes edges interconnecting nodes of the cell graph (lower graph) for level i=1 and nodes of the tissue parts graph for level i=2. These edges (hierarchical edges) represent hierarchical relations between nodes of the two entity graphs. In particular, if the cell represented by a node in the cell graph $EG_1$ spatially belongs to the tissue-part represented by a node in graph $EG_2$, then a hierarchical edge is defined between these two nodes. Hierarchical edges thus indicate hierarchical correspondence between nodes of the two entity graphs.

Figure 5:
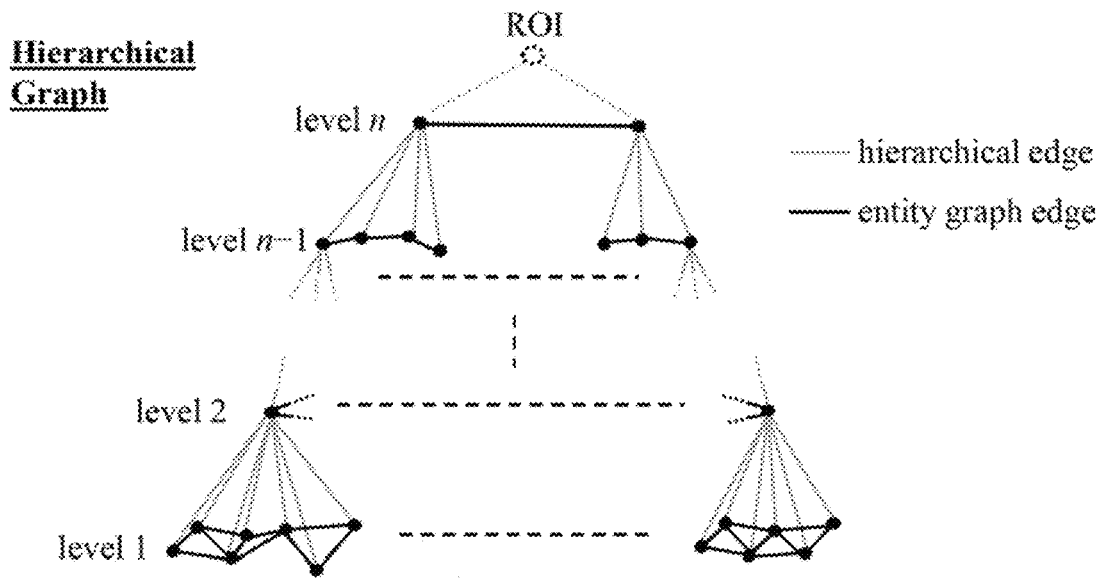

The principles described above can be applied to construct hierarchical graphs spanning multiple magnification levels of an ROI. This is illustrated schematically in FIG. 5 for levels i=1 to n of a multilevel hierarchical graph for an ROI (represented by the implicit, uppermost node indicated in dotted lines in the figure). The resulting hierarchical graph for an ROI can thus encode information extracted from the WSI across the entirety of the hierarchical tissue structure, not just cell organization as in prior schemes. Biological entities represented by nodes of hierarchical graphs may comprise entities across all scales, including nuclei, cells, different tissue parts (e.g., epithelium, stroma, necrosis, lumen structures, muscle, fat, etc.), whole tissues and glands. Entity graph edges capture local level interactions, and hierarchical edges capture hierarchical tissue information. The hierarchical representation thus captures entity-based, multi-level hierarchical tissue attributes similar to pathological diagnostic procedure, and can seamlessly scale to any sized ROI to incorporate local and global context information for improved stratification.

Figure 6:
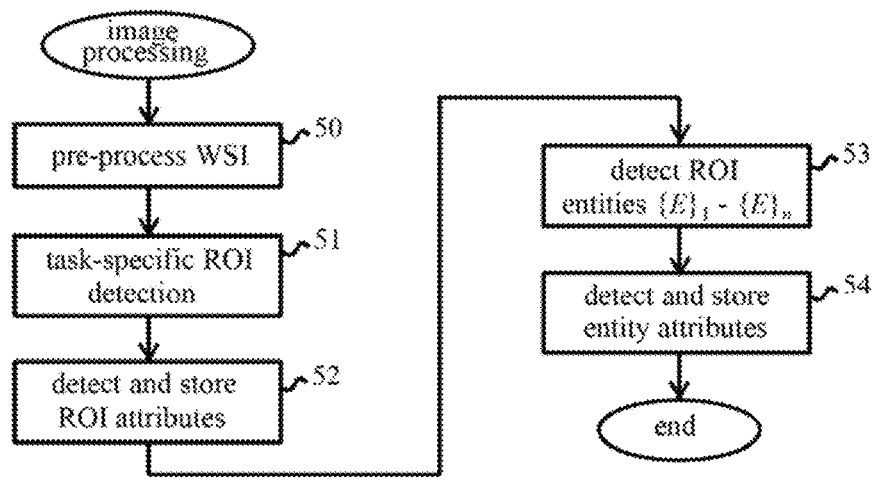
FIG. 6 is a flowchart illustrating more detailed operation of image processing logic according to at least one embodiment of the FIG. 2 system.

Preferred embodiments of computing system 20 will now be described in more detail. FIG. 6 indicates operation of image processor 23 in a preferred system. In step 50, the image processor pre-processes the WSI in generally known manner. Such preprocessing is task-specific (i.e., dependent on the particular evaluation to be performed for a given specimen) and involves standard processes such as stain normalization to remove staining variance across images, background removal, tissue area detection to bound regions of evaluation, and so on. Subsequently, in step 51, task-specific ROIs are identified based on predetermined detection criteria following pathological heuristics.

In step 52, the image processor 23 makes measurements in the image to determine particular features, or attributes, of the ROIs. In particular, spatial location of each ROI is determined, and potentially also other attributes (such as features relating to shape, color, texture, etc.) of the ROI. The resulting set of attributes for each ROI can be defined by a vector (referred to herein as a "feature vector") of the measured features. The ROI feature vectors are stored in system memory 21 for use as later described.

In step 53, for each ROI, the image processor detects the sets of biological entities $\{E\}_1$ to $\{E\}_n$ which are apparent in that region at respective magnification levels. For a given evaluation task, relevant biological entities can be detected based on pathological prior knowledge. The entities detected at different magnification levels can be defined in various ways. For example, while the entities in FIG. 4a are cells, in FIG. 4b the entities are tissue parts defined by so-called "superpixels". The FIG. 4b example was obtained in this embodiment using an SLIC (Simple Linear Iterative Clustering) algorithm (as described in "Slic superpixels compared to state-of-the-art superpixel methods", R. Achanta et al., IEEE transactions on pattern analysis and machine intelligence, vol. 34, no. 11, pp. 2274-2282) emphasizing space proximity to over-segment tissue parts into non-overlapping homogeneous superpixels. To create superpixels capturing meaningful tissue information, adjacent similar superpixels were merged, where similarity was measured by various texture attributes such as contrast, dissimilarity, homogeneity, energy, and channel-wise color attributes (standard deviation, median, energy and skewness from an 8-bin color histogram). Entities in successive, lower magnification levels may be defined by larger areas, e.g., larger superpixels, up to boundaries of whole tissues.

In step 54, the image processor makes measurements for entities in each set $\{E\}_i$ to determine attributes of each entity. Entities are spatially encoded here by their spatial centroids normalized by the image size. As well as spatial location, attributes in this embodiment include features relating to shape and texture of the entity. For the FIG. 4a example, shape features included eccentricity, area, maximum and minimum length of axis, perimeter, solidity and orientation of cells. Texture features included average foreground and background difference, standard deviation, skewness and mean entropy of intensity, as well as dissimilarity, homogeneity, energy and ASM (Active Shape Models) from a Gray-Level Co-occurrence Matrix as defined in the Zhou et al., reference above. For the FIG. 4b example, superpixel attributes included spatial location along with various color and texture features as described above. Selected features were also applied to an ML model, here a RF (Random Forests) model pretrained to classify tissue parts by tissue type (here epithelium, stroma, necrosis and background tissue) as an additional attribute. The resulting set of attributes for each entity in sets $\{E\}_1$ to $\{E\}_n$ is defined by a corresponding feature vector. The entity feature vectors are stored, in step 54, in the entity data 31 for each magnification level, and the image processing operation is complete.

The entity graphs and hierarchical graph for each ROI are generated generally as described above. In this embodiment, edges of the FIG. 4a cell graph were obtained by using a kNN (k-nearest neighbor) search to insert edges to the nearest neighbors of each cell, and then pruning edges longer than a distance threshold. At lower magnification levels, such as for superpixels in FIG. 4b, it can be assumed that adjacent tissue parts biologically interact and should be connected by edges. In each entity graph, presence or absence of an edge between nodes can be defined by an N-by-N adjacency matrix with binary elements, where N is the number of nodes in the graph, and a "1" at position (p, q) in the matrix signifies an edge between node p and node q. The resulting entity graph for each magnification level is then fully defined by this adjacency matrix and a matrix of the feature vectors, described above, for respective nodes of the graph. The hierarchical graph is then defined by this entity graph data and additional data defining the hierarchical edges. In particular, hierarchical edges between two entity graphs $EG_i$, and $EG_{i+1}$ for successive magnification levels can be defined by a binary assignment matrix of dimension $N_i$-by-$N_{i+1}$, where $N_i$ is the number of nodes in $EG_i$, $N_{i+1}$ is the number of nodes in $EG_{i+1}$, and a "1" at position (p, q) in this matrix indicates a hierarchical edge between node p in $EG_i$ and node q in $EG_{i+1}$. The hierarchical graph for an ROI is thus defined by the entity graph data for constituent entity graphs, and the assignment matrices for hierarchical edges between these graphs.

Figure 7:
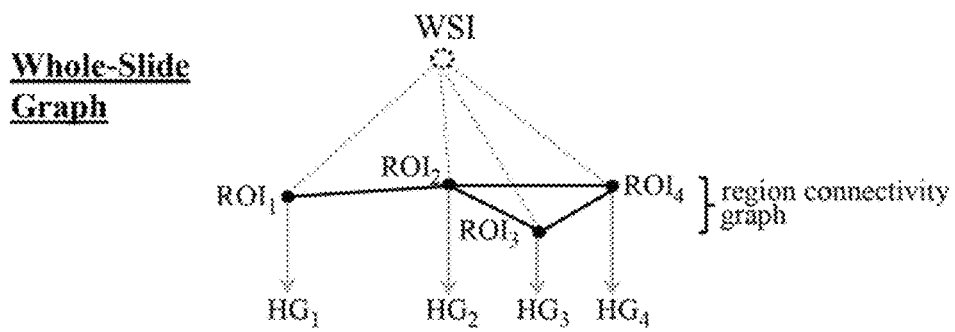
FIG. 7 illustrates construction of a whole-slide graph according to at least one embodiment.

In this preferred embodiment, the system control logic includes a whole-slide graph generator 27 which is adapted to generate a whole-slide graph (WSG) encompassing all ROIs in the WSI. Construction of this graph in WSG generator 27 is illustrated schematically in FIG. 7. The WSG generator 27 generates a region connectivity graph comprising nodes, representing respective ROIs, interconnected by edges representing spatial relations between these ROIs. FIG. 7 shows nodes, labeled $ROI_1$ to $ROI_4$, and edges of a region connectivity graph for a simple WSI (represented by the implicit, uppermost WSG node indicated in dotted lines in the figure). Each ROI node is defined by the ROI feature vector stored in step 52 of FIG. 6. Edges in the region connectivity graph may be assigned in various ways to indicate spatial relations, e.g., based on distance between ROIs as described for other edges above. In a simple example, contiguous ROIs, or ROIs whose locations are within a threshold distance, may be connected by edges in the graph. As indicated schematically in FIG. 7, the hierarchical graph (FIG. 5) for each ROI is then associated with the corresponding ROI node in the region connectivity graph to obtain the whole-slide graph for the WSI. The full WSG is defined by the ROI node data, their corresponding hierarchical graphs, and the adjacency matrix for the region connectivity graph. The resulting WSG data 34 is then stored in system memory 21.

Figure 8:
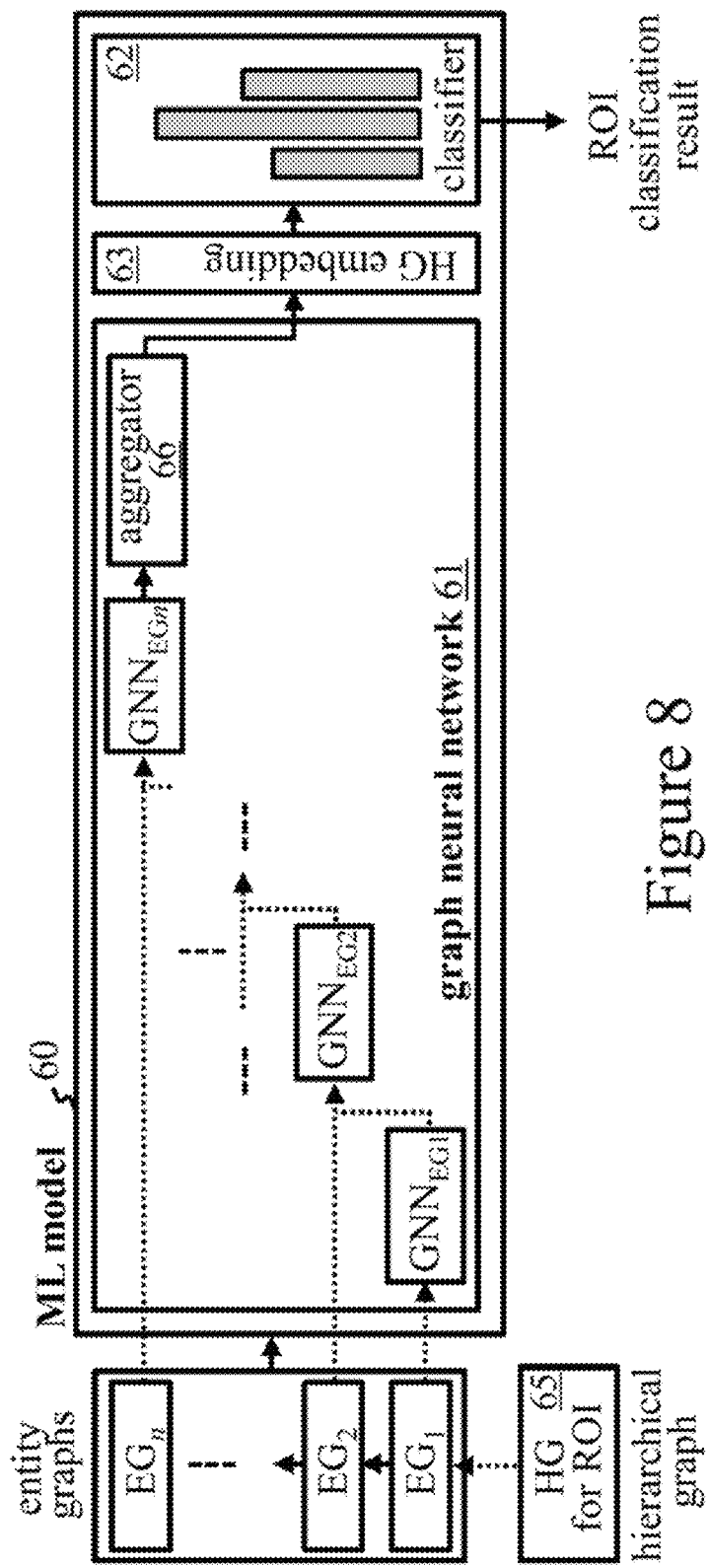
FIGS. 8 and 9 illustrate AI system architectures according to embodiments of the FIG. 2 system.

FIG. 8 illustrates an embodiment of AI system 26 which is adapted to process the hierarchical graph HG for an individual ROI. In this embodiment, the AI system comprises a pre-trained ML model 60 comprising a graph neural network 61 and an evaluator which is implemented by an ML classifier 62. The graph neural network 61 is adapted to process the hierarchical graph HG for an ROI to produce embedded data 63 representing the hierarchical graph. Classifier 62 is adapted to map the embedded data to result data indicating a medical classification (e.g., tumor-type) for the ROI.

In operation of pre-trained ML model 60, the hierarchical graph 65 for an ROI is supplied to graph neural network 61. The hierarchical graph HG defines a hierarchy of entity graphs, $EG_1$ to $EG_n$, as described above. The graph neural network (GNN) 61 comprises a plurality of entity graph networks, labeled $GNN_{EG1}$ to $GNN_{EGn}$, for receiving respective entity graphs $EG_1$ to $EG_n$ of HG 65. Each entity graph network $GNN_{EGi}$ comprises a multilayer GNN. This GNN may be implemented, for example, by a message passing neural network. In this preferred embodiment, each entity graph network $GNN_{EGi}$ comprises a Graph Isomorphism Network as described in "How powerful are graph neural networks?", K. Xu et al., International Conference on Learning Representations, ICLR, 2019. Each entity graph network $GNN_{EGi}$ receives the graph data for the corresponding entity graph $EG_i$, and produces node embeddings for respective nodes of this entity graph. As illustrated in FIG. 8, the entity graph networks $GNN_{EG1}$ to $GNN_{EGn}$ are connected in succession in order of the hierarchy of entity graphs from highest to lowest magnification level i=1 to n. The node embeddings produced for an entity graph by an entity graph network are assigned to nodes of the entity graph supplied to the next entity graph network according to the hierarchical edges linking nodes of those entity graphs. In particular, each entity graph network after $GNN_{EG1}$, i.e. $GNN_{EG2}$ to $GNN_{EGn}$, also receives the assignment matrix defining hierarchical edges between its input entity graph $EG_i$ and the preceding entity graph $EG_{i-1}$ in the HG hierarchy. Each of these entity graph networks $GNN_{EG2}$ to $GNN_{EGn}$ assigns the node embeddings produced by the preceding entity graph network to nodes of its input entity graph along hierarchical edges linking nodes of these two entity graphs (as defined by the input assignment matrix). Node embeddings assigned to a given node are added to (e.g. concatenated or otherwise combined with) the input feature vector for that node. As the entity graphs $EG_1$ to $EG_n$ are successively processed by $GNN_{EG2}$ to $GNN_{EGn}$, the hierarchical graph information is thus progressively embedded in the outputs of these entity graph networks. The node embeddings output by the last entity graph network $GNN_{EGn}$ thus embed all information in the hierarchical graph HG.

The node embeddings output by $GNN_{EGn}$ are aggregated (e.g., concatenated or otherwise combined) in an aggregator module 66 to produce the final embedded data, HG embedding 63, representing the input hierarchical graph. The HG embedding 63 is supplied to classifier 62 to obtain a region-specific classification for the ROI represented by HG 65.

While pre-trained ML model 60 is adapted to process the hierarchical graph for a single region of interest, hierarchical graphs for multiple ROIs may of course be supplied in succession to pre-trained ML model 60 to obtain results for each ROI. An overall result for a specimen might additionally be obtained by processing all resulting ROI classifications. For example, a rule-based system might be provided for producing a final result based on all ROI results. In other embodiments, multiple pre-trained ML models 60 may be provided for parallel processing of HGs for multiple ROIs. A particularly preferred implementation of AI system 26 for processing multiple ROIs is illustrated schematically in FIG. 9.

Figure 9:
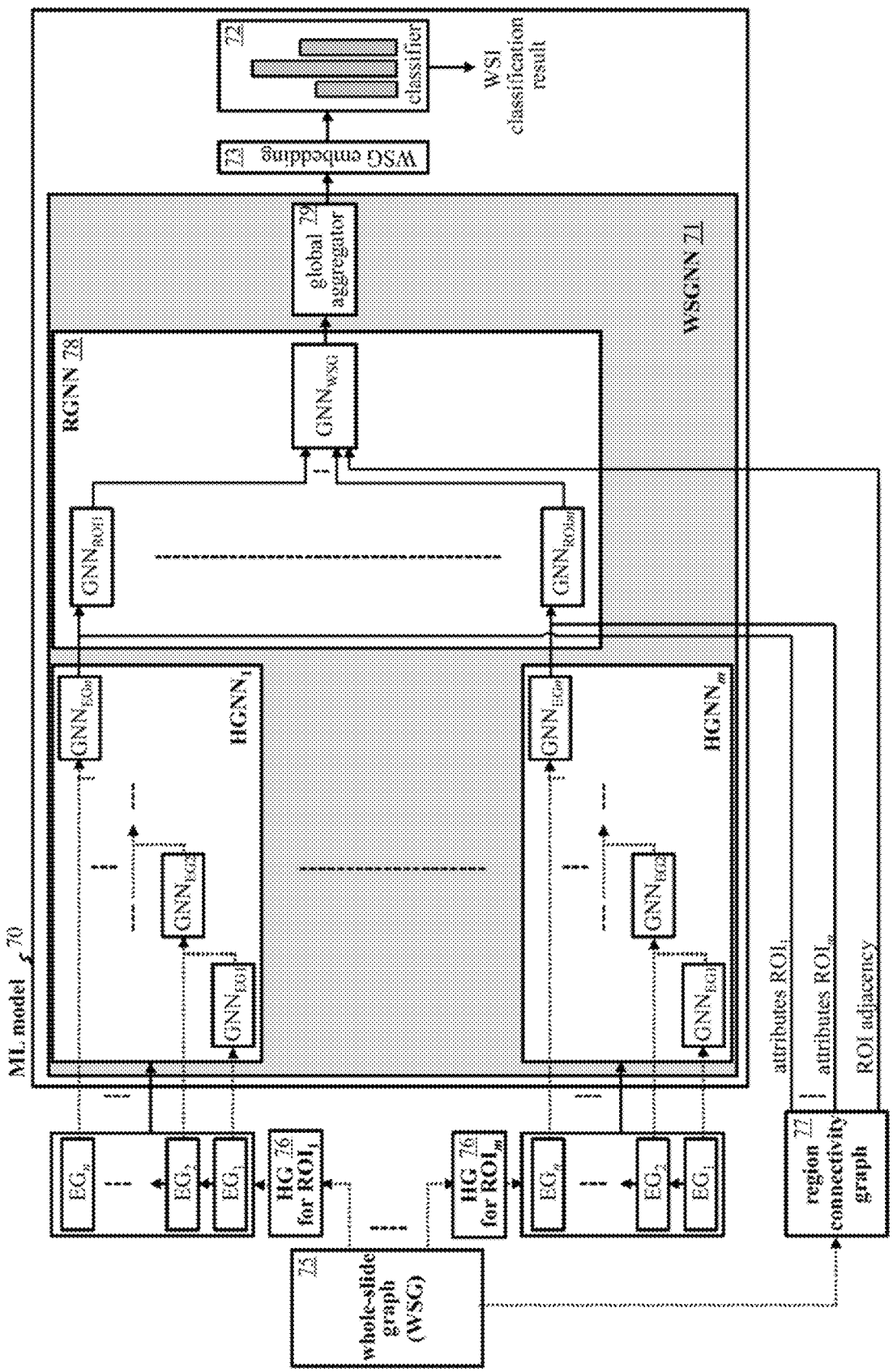

The AI system of FIG. 9 comprises a pre-trained ML model 70 comprising a graph neural network 71 and an evaluator which is again implemented by an ML classifier 72. The graph neural network (WSGNN) 71 is adapted to process a whole-slide graph (FIG. 7) to produce embedded data 73 representing the WSG. Classifier 72 is adapted to map the embedded data to result data indicating a medical classification (e.g., cancer sub-type) for the WSG.

In operation of pre-trained ML model 70, the whole-slide graph 75 is supplied to WSGNN 71. The whole-slide graph WSG includes hierarchical graphs 76 for a plurality of ROIs, and a region connectivity graph 77 as described above. The WSGNN 71 comprises a plurality of hierarchical graph networks, labeled $HGNN_1$ to $HGNN_m$, for receiving respective hierarchical graphs HG of the whole-slide graph. Each hierarchical graph network $HGNN_1$ to $HGNN_m$ comprises a plurality of entity graph networks $GNN_{EG1}$ to $GNN_{EGn}$ which are arranged for operation generally as described above for GNN 61 of FIG. 8. (Note that, in practice, n may be different for different $HGNN_s$). The entity graph networks $GNN_{EG1}$ to $GNN_{EGn}$ of an HGNN receive respective entity graphs of the input hierarchical graph HG for a particular region of interest $ROI_1$ to $ROI_m$. Each HGNN thus outputs node embeddings for the corresponding hierarchical graph HG.

WSGNN 71 also includes a region graph network (RGNN) 78 which is adapted to process the region connectivity graph 77 to produce node embeddings for respective nodes thereof. RGNN 78 comprises a plurality of GNNs, labeled $GNN_{ROI1}$ to $GNN_{ROIm}$, which receive the node embeddings from respective networks $HGNN_1$ to $HGNN_m$. In particular, the node embeddings produced by networks $HGNN_1$ to $HGNN_m$ from HGs 76 are assigned to the nodes of region connectivity graph 77 which are associated with those HGs in the whole-slide graph. These HG node embeddings are combined (e.g., concatenated) with the ROI feature vectors for the corresponding ROI nodes for input to respective networks $GNN_{ROI1}$ to $GNN_{ROIm}$. The resulting, embedded ROI vectors output by $GNN_{ROI1}$ to $GNN_{ROIm}$ are supplied, along with the adjacency matrix of region connectivity graph 77, to a further GNN, labeled $GNN_{WSG}$, of RGNN 78. The resulting ROI node embeddings output by $GNN_{WSG}$, are then aggregated (e.g. concatenated or otherwise combined) in an aggregator module 79 to produce the final embedded data, WSG embedding 73, representing the whole-slide graph. The WSG embedding 73 is supplied to classifier 72 to obtain a classification result for the WSI as a whole.

The embodiments of FIGS. 8 and 9 provide efficient and powerful models for interpreting hierarchical graphs. The framework scales readily to giga-pixel sized WSIs, offering evaluation at region or whole-slide level based on all hierarchical tissue information encoded in the graphs. The hierarchical graph representation provides control over the model input, and aligns closely with the established clinical diagnostic procedure for multi-resolution tissue analysis. The ML systems can be guided to specific biological entities by pathological prior knowledge, and can learn the importance of fine, course, and hierarchical feature information for correct interpretation of WSIs. The enriched multi-level topological representation and hierarchical learning have been demonstrated to give superior classification performance. The methodology has been tested on a large set of annotated tissue ROIs from breast-carcinoma whole-slides, and outperformed recent convolutional neural network and graph neural network approaches for multi-class cancer subtyping.

Figure 10:
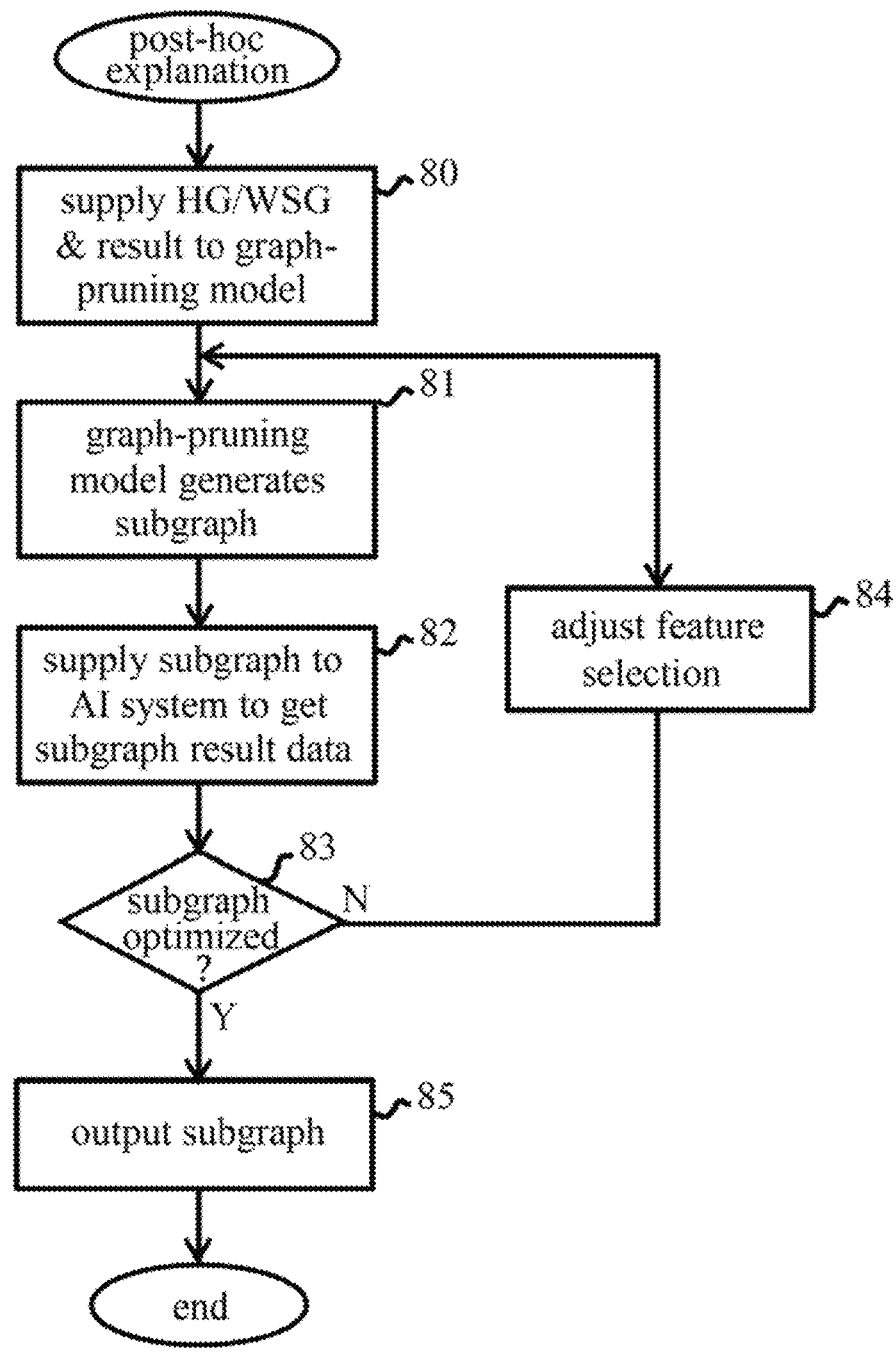
FIG. 10 is a flowchart illustrating operation of a graph pruning model according to at least one embodiment of the system.

Preferred embodiments of computing system 20 also offer post-hoc explanation of the results from AI system 26. FIG. 10 illustrates operation of graph-pruning model 28 which implements the post-hoc explainer in preferred computing systems 20. After processing an HG or WSG to obtain an evaluation result in AI system 26, in step 80 of FIG. 10 the graph (HG or WSG as appropriate) is supplied to graph-pruning model 28, along with the associated result data. Graph pruning model 28 is adapted to process the input graph to produce a minimized subgraph which, when supplied to AI system 26, produces subgraph result data which correlates maximally with the original result data. This is an optimization problem which is represented schematically by steps 81 to 84 of FIG. 10. In step 81, the graph pruning model selects a subset of the graph features (i.e., nodes, attributes from node feature vectors where provided, edges, and hierarchical edges) to produce a subgraph. The resulting subgraph is then supplied, in step 82, to AI system 26 to obtain result data for the subgraph. In decision step 83, the graph-pruning model 28 decides if the optimization criterion has been met. This criterion requires the subgraph size to be minimized, and the mutual information between the subgraph result data and the result for the original graph to be maximized. If the optimization condition is not met, the feature selection process is modified in step 84 and operation reverts to step 81 where a new subgraph is generated. The operation thus iterates, progressively modifying the subgraph generation procedure to move towards the optimization condition as the model learns which features are most important for satisfying this condition. When it is decided that the subgraph has been optimized at step 83, the optimal subgraph is output in step 85, and the process is complete.

Mathematically, the above process involves pruning the graph representation (HG or WSG) by removing redundant or non-informative nodes and edges such that the (non-interpretable) AI prediction remains as close as possible to the original prediction and the subgraph is as small as possible. As will be apparent to those skilled in the art, graph-pruning model 28 may use various algorithms, e.g., to fit a neural network, to find the optimal subgraph. For example, the model may leverage recent advances in interpretability over graph data as described in "GNNExplainer: Generating Explanations for Graph Neural Networks", Ying et al., NeurIPS 2019. Maximizing mutual information between the subgraph and the original prediction can be achieved by learning activation and deactivation masks for nodes and edges. To obtain the optimal compressed subgraph, the masks must be maximally sparsified without compromising the prediction performance. The resulting subgraph then presents a relevant subset of the original hierarchical (HG or WSG) representation that drives the predicted outcome for that representation. This subset, i.e., the subgraph, then provides the explanation for the AI-generated result. The subgraph is considered useful if the subset of biological entities and interactions correspond to pathological comprehension. Where there is agreement between pathologists and the explanation provided by such subgraphs, the subgraphs may be used to further train the AI model 26 to enhance model operation.

It will be seen that the above embodiments offer powerful systems for AI-assisted, interpretable decision support in digital pathology through hierarchical representation of tissue specimens. It will be appreciated, however, that numerous changes and modifications can be made to the exemplary embodiments described. By way of example, other techniques, both probabilistic and deterministic, may be used to insert edges in graphs based on distance metrics and/or pathological prior knowledge. Edges may also have attributes, e.g. weights dependent on some distance metric, in other embodiments.

AI system 26 may be implemented by other processing systems that accept graphs as input, and evaluator 63, 73 of such systems may comprise one or a combination of classification and regression models in other embodiments. Multi-modal information may also be integrated with the hierarchical tissue representation, e.g. by concatenating results from different analysis procedures (e.g. gene expression data, images from different biomarkers such as ER, PR, HER2, etc.) with node embeddings at the appropriate hierarchy level of a WSG.

In general, where features are described herein with reference to a method embodying the invention, corresponding features may be provided in a system/computer program product embodying the invention, and vice versa.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 11:
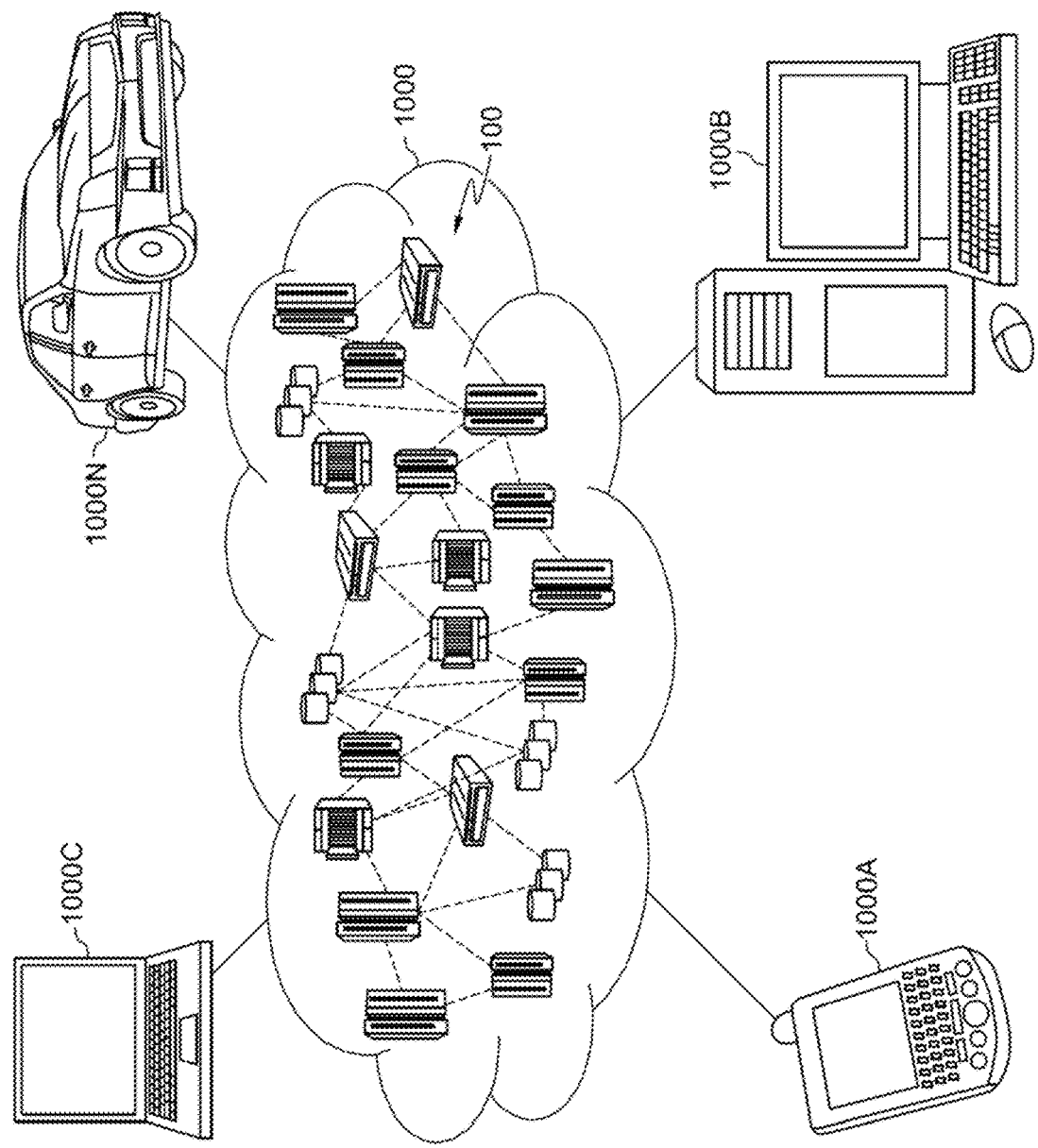
FIG. 11 is a block diagram of an illustrative cloud computing environment including the computer system depicted in FIG. 1, in accordance with an embodiment of the present disclosure.

Referring now to FIG. 11, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 11 are intended to be illustrative only and that computing nodes 100 and cloud computing environment 1000 can communicate with any type of computerized device over any type of network and/or network addressable connection (e.g., using a web browser).

Figure 12:
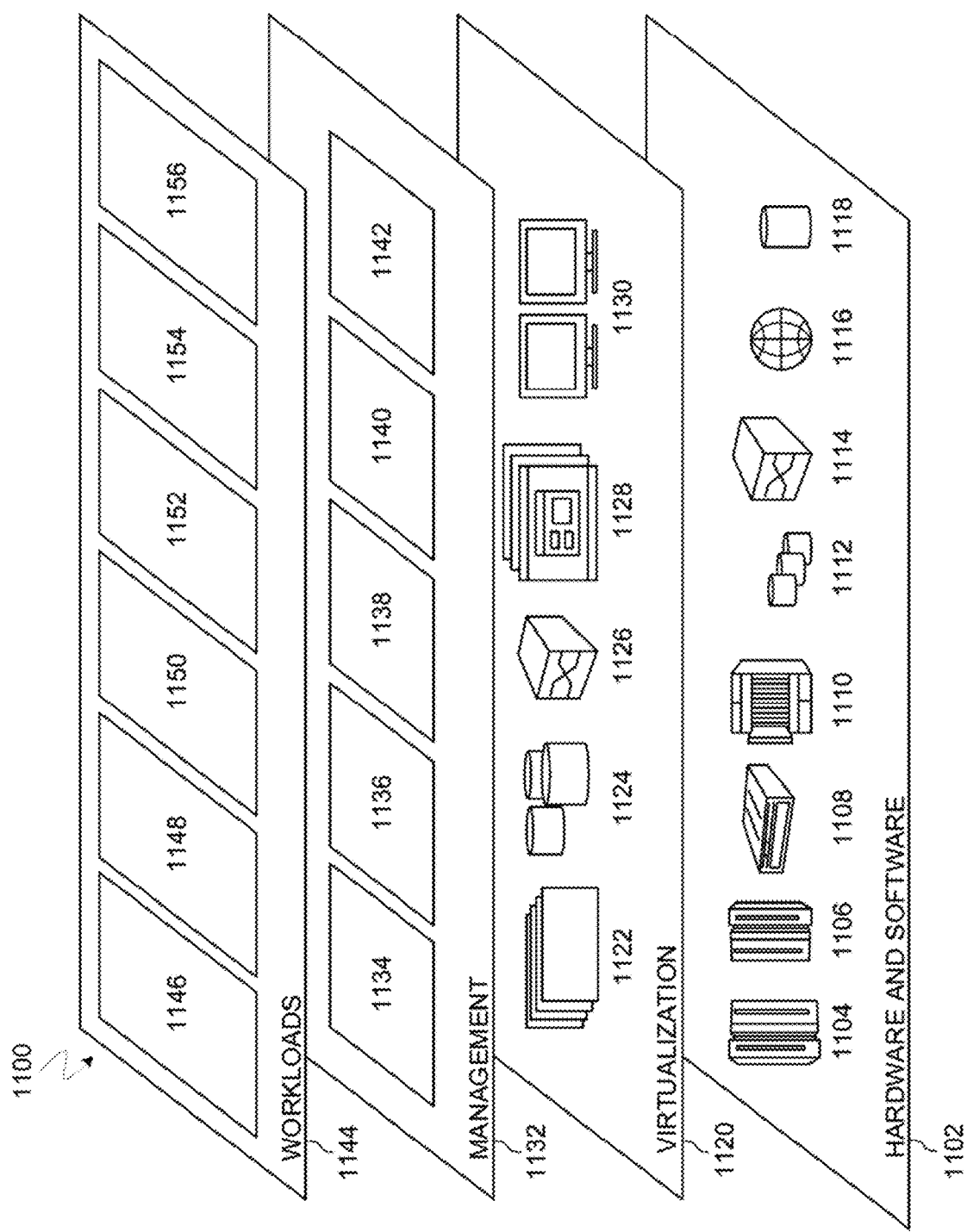
FIG. 12 is a block diagram of functional layers of the illustrative cloud computing environment of FIG. 11, in accordance with an embodiment of the present disclosure.

Referring now to FIG. 12, a set of functional abstraction layers 1100 provided by cloud computing environment 1000 is shown. It should be understood in advance that the components, layers, and functions shown in FIG. 12 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and whole slide image interpretation 1156. A whole slide image interpretation program provides a way to automatically and consistently interpret whole-slide images of tissue specimens by employing artificial intelligence.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises," "comprising," "includes," "including," "has," "have," "having," "with," and the like, when used in this specification, specify the presence of stated features, integers, steps, operations, elements, and/or components, but does not preclude the presence or addition of one or more other features, integers, steps, operations, elements, components, and/or groups thereof.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for interpreting a whole-slide image of a tissue specimen, the method comprising:
   for at least one region of interest in the tissue specimen, detecting biological entities in that region independently at each of a plurality of magnification levels in the whole-slide image and, for each magnification level, generating an entity graph comprising nodes, representing respective biological entities detected at that magnification level, interconnected by edges representing interactions between entities represented by the nodes;
   for each region of interest of the at least one region of interest, generating a hierarchical graph, defining a hierarchy of the entity graphs for that region of interest, in which nodes of different entity graphs are interconnected by hierarchical edges representing hierarchical relations between nodes of the entity graphs for the region of interest;
   supplying the hierarchical graph for the at least one region of interest to an AI system which is adapted to process such hierarchical graphs to produce result data corresponding to a medical evaluation of the tissue specimen represented thereby; and
   outputting the result data for the tissue specimen.

2. The computer-implemented method of claim 1 wherein the AI system is adapted to process the hierarchical graph for a single region of interest, the method including, for each region of interest, supplying the hierarchical graph for that region of interest to the AI system to obtain the result data corresponding to a medical evaluation of that region of interest of the tissue specimen.

3. The computer-implemented method of claim 2 wherein, for each region of interest:
   supplying the hierarchical graph and the result data for that region of interest to a graph pruning model which is adapted to process the hierarchical graph to produce a minimized subgraph which, when supplied to the AI system, produces subgraph result data which correlates maximally with the result data for the hierarchical graph.

4. The computer-implemented method of claim 3, further comprising:
   performing the processing of the hierarchical graph in the graph pruning model.

5. The computer-implemented method of claim 1, further comprising:
   generating the hierarchical graph for each region of interest of the at least one region of interest;
   generating a region connectivity graph comprising region of interest (ROI) nodes, wherein the ROI nodes represent respective regions of interest, interconnected by relation edges representing spatial relations between the respective regions of interest represented by those ROI nodes;
   generating a whole-slide graph in which the hierarchical graph for each region of interest is associated with the ROI node representing that region of interest in the region connectivity graph; and
   supplying the whole-slide graph to the AI system, wherein the AI system is adapted to process the whole-slide graph to produce the result data corresponding to a medical evaluation of the whole-slide image of the tissue specimen.

6. The computer-implemented method of claim 5, further comprising:
   supplying the whole-slide graph and the result data for the whole-slide image to a graph pruning model which is adapted to process the whole-slide graph to produce a minimized subgraph which, when supplied to the AI system, produces subgraph result data which correlates maximally with the result data for the whole-slide image.

7. The computer-implemented method of claim 6, further comprising:
   performing the processing of the whole-slide graph in the graph pruning model.

8. The computer-implemented method of claim 1, further comprising:
   performing the processing of the hierarchical graph in the AI system.

9. The computer-implemented method of claim 8 wherein the AI system comprises a pre-trained machine learning model.

10. The computer-implemented method of claim 1 wherein the entity graph includes a feature vector for each node of the entity graph, the feature vector defining a set of attributes of a biological entity represented by that node.

11. The computer-implemented method of claim 1 wherein the edges in the entity graph are defined in dependence on distance between detected entities represented by the nodes of the entity graph.

12. The computer-implemented method of claim 1 wherein the biological entities represented by nodes of the hierarchical graph comprise a plurality of entities selected from the group consisting of: nuclei, cells, tissue parts, glands and whole tissues.

13. The computer-implemented method of claim 1, further comprising:
   pre-processing the whole-slide image to detect the at least one region of interest in the tissue specimen.

14. A computing system for interpreting a whole-slide image of a tissue specimen, the system comprising:
   memory for storing the whole-slide image;
   image processing logic adapted, for at least one region of interest in the tissue specimen, to detect biological entities in that region independently at each of a plurality of magnification levels in the whole-slide image;

entity graph logic adapted, for each magnification level, to generate an entity graph comprising nodes, representing respective biological entities detected at that magnification level, interconnected by edges representing interactions between entities represented by the nodes;

hierarchical graph logic adapted, for each region of interest of the at least one region of interest, to generate a hierarchical graph, defining a hierarchy of the entity graphs for that region of interest, in which nodes of different entity graphs are interconnected by hierarchical edges representing hierarchical relations between nodes of the entity graphs for the region of interest; and an AI system which is adapted to process the hierarchical graph for the at least one region of interest to produce result data corresponding to a medical evaluation of the tissue specimen represented thereby, and to output the result data for the tissue specimen.

15. The computer system of claim 14 wherein the AI system is adapted to process the hierarchical graph for each region of interest to produce the result data corresponding to a medical evaluation of that region of interest of the tissue specimen.

16. The computer system of claim 15 wherein the AI system comprises a pre-trained machine learning model comprising:
a graph neural network adapted to process the hierarchical graph for the region of interest to produce embedded data representing the hierarchical graph; and
an evaluator adapted to map the embedded data to the result data for the region.

17. The computer system of claim 16 wherein:
the graph neural network comprises a plurality of entity graph networks for receiving respective entity graphs of the hierarchical graph, each entity graph network being adapted to produce node embeddings for respective nodes of the corresponding entity graph;
the entity graph networks are connected in succession in order of the hierarchy of entity graphs from highest to lowest magnification level of the entity graphs;
the node embeddings produced for the entity graph by an entity graph network are assigned to nodes of the entity graph supplied to the next entity graph network according to the hierarchical edges linking nodes of those entity graphs; and
the node embeddings produced by the last entity graph network in the succession are combined to produce the embedded data representing the hierarchical graph.

18. The computer system of claim 15, wherein the system includes a graph pruning model for receiving the hierarchical graph for each region of interest and the result data for that region of interest, the graph pruning model being adapted to process the hierarchical graph to produce a minimized subgraph which, when supplied to the AI system, produces subgraph result data which correlates maximally with the result data for the hierarchical graph.

19. The computer system of claim 14 wherein:
the computing system is adapted to generate a said hierarchical graph for each region of interest of a plurality of regions of interest;
the computing system includes whole-slide graph logic adapted to generate a region connectivity graph comprising region of interest (ROI) nodes, representing respective regions of interest, interconnected by relation edges representing spatial relations between the respective regions of interest represented by those ROI nodes, and a whole-slide graph in which the hierarchical graph for each region of interest is associated with the ROI node representing that region of interest in the region connectivity graph; and
the AI system is adapted to process the whole-slide graph to produce the result data corresponding to a medical evaluation of the whole-slide image of the tissue specimen.

20. The computer system of claim 19 wherein the AI system comprises a pre-trained machine learning model comprising:
a graph neural network adapted to process the whole-slide graph to produce embedded data representing the whole-slide graph; and
an evaluator adapted to map the embedded data to said result data for the whole-slide image.

21. The computer system of claim 20 wherein:
the graph neural network comprises a plurality of hierarchical graph networks for receiving respective hierarchical graphs of the whole-slide graph;
each hierarchical graph network comprises a plurality of entity graph networks for receiving respective entity graphs of the hierarchical graph, each entity graph network being adapted to produce node embeddings for respective nodes of the corresponding entity graph;
in each hierarchical graph network, the entity graph networks are connected in succession in order of the hierarchy of entity graphs from highest to lowest magnification level of the entity graphs;
in each hierarchical graph network, the node embeddings produced for an entity graph by an entity graph network are assigned to nodes of the entity graph supplied to a next entity graph network according to the hierarchical edges linking nodes of those entity graphs;
the node embeddings produced from each hierarchical graph by a last entity graph network in the succession are assigned to the node of the region connectivity graph which is associated with that hierarchical graph in the whole-slide graph;
the graph neural network further comprises a region graph network adapted to process the region connectivity graph to produce region connectivity node embeddings for respective nodes thereof; and
the region connectivity node embeddings produced from the region connectivity graph are combined to produce the embedded data representing the whole-slide graph.

22. The computer system of claim 19, wherein the system includes a graph pruning model for receiving the whole-slide graph and the result data for the whole-slide image, the graph pruning model being adapted to process the whole-slide graph to produce a minimized subgraph which, when supplied to the AI system, produces subgraph result data which correlates maximally with the result data for the whole-slide image.

23. A computer program product for interpreting a whole-slide image of a tissue specimen, said computer program product comprising a computer readable storage medium having program instructions embodied therein, the program instructions being executable by a computing system to cause the computing system to:
for at least one region of interest in the tissue specimen, detect biological entities in that region independently at each of a plurality of magnification levels in the whole-slide image and, for each magnification level, generate an entity graph comprising nodes, representing respective biological entities detected at that magnification level, interconnected by edges representing interactions between entities represented by the nodes;

for each region of interest, generate a hierarchical graph, defining a hierarchy of the entity graphs for that region of interest, in which nodes of different entity graphs are interconnected by hierarchical edges representing hierarchical relations between nodes of the entity graphs for the region of interest;

supply the hierarchical graph for said at least one region of interest to an AI system which is adapted to process such hierarchical graphs to produce result data corresponding to a medical evaluation of the tissue specimen represented thereby; and output the result data for the tissue specimen.

24. The computer program product of claim 23, wherein the program instructions are further executable to cause the computing system to implement the AI system.

25. The computer program product of claim 23, wherein the program instructions are further executable to cause the computing system to implement a graph pruning model for receiving the result data for the tissue specimen, the graph pruning model being adapted to process the hierarchical graph for the at least one region of interest to produce a minimized subgraph which, when supplied to the AI system, produces subgraph result data which correlates maximally with the result data for the tissue specimen.

* * * * *